US00PP35272P2

(12) United States Plant Patent
Hansen

(10) Patent No.: US PP35,272 P2
(45) Date of Patent: Jul. 18, 2023

(54) ***ECHINACEA* PLANT NAMED 'BUTTER PECAN'**

(50) Latin Name: ***Echinacea* hybrid**
Varietal Denomination: Butter Pecan

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,773

(22) Filed: Nov. 16, 2022

(51) Int. Cl.
*A01H 5/02* (2018.01)

(52) U.S. Cl.
USPC ..... Plt./428

(58) Field of Classification Search
USPC ..... Plt./428
See application file for complete search history.

*Primary Examiner* — Susan McCormick Ewoldt

(57) ABSTRACT

The new and distinct cultivar of *Echinacea* plant named 'Butter Pecan' with inflorescences on branched stems producing single whorls of creamy-yellow ray florets and a large center pompon of disk florets. The disk florets are very long with notched apices and frequently with extra side lobes giving a fuller pompon effect. The new plant flowers from mid-summer to late summer, and is suitable as a potted plant, for the landscape, and for cut flower arrangements.

1 Drawing Sheet

Botanical denomination: *Echinacea* hybrid.
Cultivar designation: 'Butter Pecan'.

STATEMENT REGARDING PRIOR DISCLOSURES UNDER 37 CFR 1.77(B)(6)

The first non-enabling disclosures of the claimed plant, in the form of a photograph and brief description on a website operated by Walters Gardens, Inc. on Dec. 1, 2021, followed by a photograph and brief description in the "Walters Gardens 2022-2023 Catalog" on Jun. 8, 2022. The claimed plant was first sold on Aug. 1, 2022, to W.W. Greenhouses by Walters Gardens, Inc., who obtained the new plant and all information relating thereto, from the inventor. No plants of *Echinacea* 'Butter Pecan' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'Butter Pecan'. The new plant was the result of a cross by the inventor of an unnamed proprietary hybrid known as 16-104-1 (not patented) as the female parent and an unnamed proprietary hybrid known as 16-30-1 (not patented) as the male on Aug. 9, 2017, at a wholesale perennial nursery in Zeeland, Mich. The single seedling selected was evaluated initially in trials in the summer of 2018 at the same nursery and assigned the breeder code of 17-2-1.

*Echinacea* 'Butter Pecan' has been asexually propagated at the same nursery by crown division and also using careful shoot tip tissue culture procedures and found to reproduce plants that exhibit all the characteristics identical to the original plant in successive generations.

*Echinacea* 'Butter Pecan' is distinct from all other Coneflowers known to the inventor. The nearest comparison cultivars are: 'BALSCLEMC' U.S. Plant Pat. No. 27,858, 'Tnechcmy' U.S. Plant Pat. No. 31,142, 'Butterfly Kisses' U.S. Plant Pat. No. 24,458, 'Little Annie' (not patented), 'Solar Flare' U.S. Plant Pat. No. 22,133, 'Coconut Lime' U.S. Plant Pat. No. 18,617, and 'Julia' U.S. Plant Pat. No. 24,629.

The female parent plant, 16-104-1, has a single row of pinkish-purple ray florets and the habit was significantly taller with less basal branching. The male parent plant, 16-30-1, has pinkish-purple ray florets and large pinkish-purple disk florets in a pompon effect.

'BALSCLEMC' has a much taller habit and the pompon disk florets are less yellowish-green when opening and lighter yellow with maturity. 'Tnechcmy' is taller in habit, inflorescences that have shorter ray florets of a deeper yellow color, and the pompon disk florets are more orangish colored. 'Butterfly Kisses' has light pinkish-purple ray florets and a darker pompom of darker purplish-pink disk florets. 'Little Annie' has a slightly taller habit with single purple-pink ray florets and without pompon disk florets. 'Solar Flare' has a single row of ray florets that are magenta rose and without pompon disk florets. 'Coconut Lime' has a taller habit, the ray and disk florets are paler greenish-yellow and the disk florets are much smaller without the occasional side lobe. 'Julia' has a single row of ray florets that are tangerine orange.

SUMMARY OF THE INVENTION

*Echinacea* 'Butter Pecan' has not been evaluated under all possible environmental conditions. The phenotype may vary with variations in the environment including: growing temperature, available sunlight, nutrients, water, etc. without a change in the genotype of the plant. The new plant is distinct from its parents and all other *Echinacea* known to the applicant in the following combined traits:

1. Inflorescences of creamy-yellow ray florets;
2. Large disk florets of creamy-yellow;
3. Center pompon of disk florets that have notched apices and frequent side lobes causing a fuller pompon effect;
4. Vigorous growth and short, compact habit;
5. Medium-green ovate to narrowly ovate foliage.

BRIEF DESCRIPTION OF THE DRAWINGS

The photographs of 'Butter Pecan' demonstrate the overall appearance of the plant including the unique traits. The drawings of the new plant are of a two-year-old plant grown in a full-sun trial garden in Zeeland, Mich. The colors are as accurate as reasonably possible with color reproductions. Some slight variation of color may occur as a result of lighting quality, intensity, wavelength, direction, or reflection.

DETAILED DESCRIPTION OF THE PLANT

Figure 1:
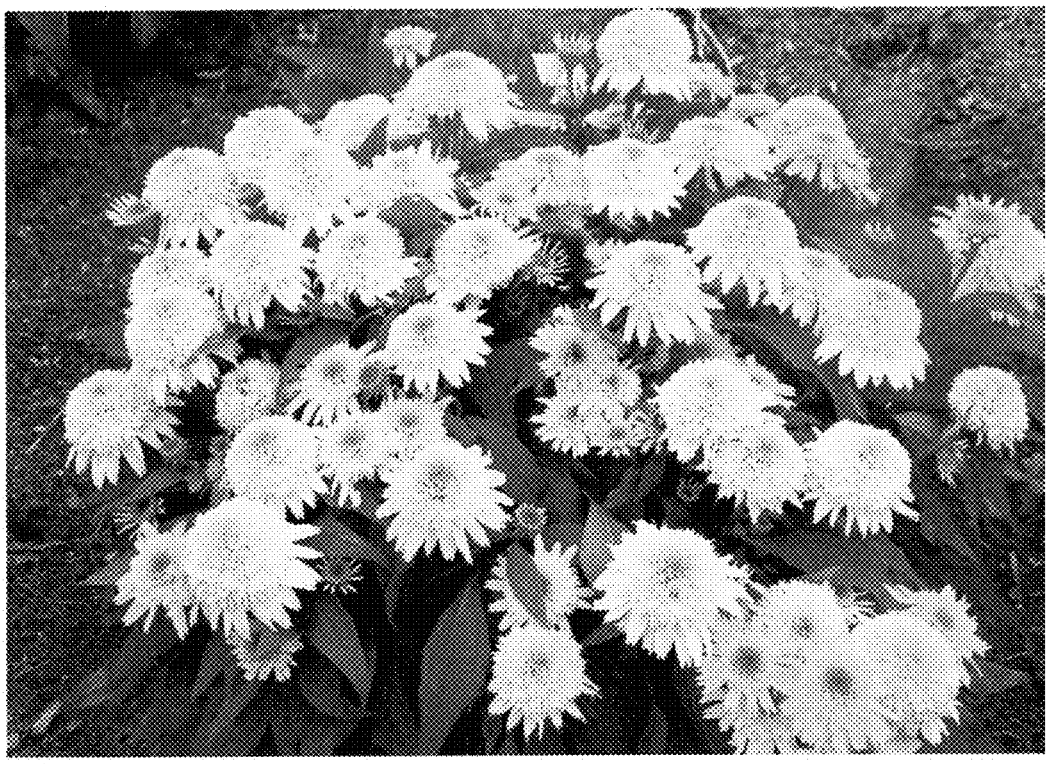
FIG. 1 shows the habit of the new plant in the flower.
Figure 2:
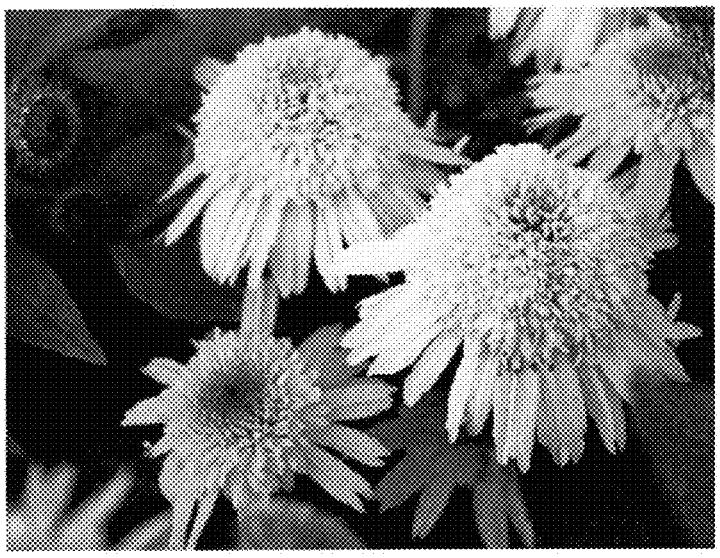
FIG. 2 shows a close-up of some inflorescences at different stages.

The following description of *Echinacea* 'Butter Pecan' is based on observations of two-year-old specimens grown in a partially-shaded greenhouse and in a full-sun trial garden in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is the proprietary unreleased hybrid 16-104-1 comprising a complex cross with 'Solar Flare' U.S. Plant Pat. No. 22,133, 'Little Annie' (not patented), and 'Butterfly Kisses' U.S. Plant Pat. No. 24,458 and male parent is the proprietary unreleased hybrid 16-30-1 comprising a complex crossing with offspring from 'Julia' U.S. Plant Pat. No. 24,629 and 'Butterfly Kisses' U.S. Plant Pat. No. 24,458;

Plant habit: Multi-stemmed, freely-branched, hardy herbaceous perennial, flowering to about 30 cm tall and 36 cm wide with foliage to 27 cm tall and 40 cm wide;

Growth rate: Vigorous, finishing in 4-liter containers in about 2 months during the summer;

Roots: Cream-colored, finely branched;

Foliage: Alternate; ovate to narrowly ovate; acute apex; cuneate base; margin micro-ciliolate and serrulate with teeth to about 0.5 mm long and 0.5 mm wide; hirsutulous abaxial and adaxial; to about 8.5 cm long and 4 cm wide decreasing distally, average about 7 cm long and 3.1 cm wide;

Leaf color: Young leaves adaxial between RHS 137B and RHS 146A, abaxial nearest RHS 137B; mature leaves adaxial nearest NN137B, abaxial between RHS 137C and RHS NN137D; variegation absent;

Foliage fragrance: Lightly herbal;

Venation: Pinnate; abaxial midrib and veins costate; glabrous adaxial, hirsutulous abaxial;

Vein color: Adaxial midrib and primary veins nearest RHS 145C, secondary nearest RHS 146D; abaxial midrib and primary veins between RHS 145A and RHS 146D, secondary nearest RHS 146D;

Petiole: Concavo-convex; glabrous adaxial; and finely hirsutulous abaxial; to about 7.5 cm long and 6 mm wide at the base on lowest leaves and decreasing to nearly sessile distally;

Petiole color: Adaxial nearest 145C, abaxial between RHS 145C and RHS 144C;

Stem: Hirsutulous; cylindrical, fistulous; strong and stiff; to about 27 cm long including peduncle and about 6.5 mm diameter at base; average 25 cm long and 6 mm diameter; about 6 to 8 per plant;

Stem color: Proximally nearest RHS 146C and distally nearest RHS 146B;

Peduncle: Hirsutulous; terete; strong; stiff; branched; about 10 cm long and 5 mm diameter above last leaves; quantity per stem about four to six; aspect ascending, upright;

Peduncle color: Proximally nearest RHS 146B;

Internode: 6 to 9 per stem; average about 3.6 cm long, shorter proximally and longer distally; node color same as surrounding peduncle;

Branches: Cylindrical; hirsutulous; tightly angled to main stem to about 60° above horizontal: about 5 to 7 branches per stem; to about 14 cm long and 3.5 mm diameter;

Branch color: Proximally nearest RHS 146B;

Inflorescence: Bracteate head, aggregate of achene; with single whorl of distinct ligulate ray florets and enlarged disk florets above pappus producing a pompon effect; flowering mid-summer to late summer; initial inflorescence largest, to about 8.5 cm wide and 5 cm tall, with inner pompon to 6.5 cm across and 5 cm tall; to 4 to 6 inflorescences per peduncle;

Inflorescence fragrance: Not observed;

Flower persistence: Remaining effective in color for 10 to 14 days depending on temperatures, cone drying on plant and effective into winter;

Involucre: With numerous bracts, about 50 to 60 per inflorescence in 3 to 4 whorls; arcuate downward toward peduncle;

Involucre bracts: Lanceolate; narrowly acute apex; truncate base; micro-ciliolate margin; adaxial glabrous to micropuberulent; abaxial hirsutulous; to about 9 mm long and 3.5 mm across decreasing distally; color adaxial center between RHS 137A and RHS 139A, abaxial nearest RHS 137A;

Inflorescence buds with ray florets vertical and still enrolled: About 25 mm across and 20 mm tall; ray floret color between RHS 145B and RHS 145C, disk florets nearest RHS 144B, and spines nearest RHS 153C;

Ray florets: Ligulate; zygomorphic; arrangement in single whorl, frequently moderately imbricate; apex emarginated with two notches to 6 mm deep and an occasional side lobe to 12 mm long and 3.5 mm wide; base attenuate; margin entire; adaxial and abaxial surfaces matte; 14 to 18 per inflorescence; opening to horizontal, drooping up to 30 degrees below horizontal with maturity; flat, twisting absent; sterile; ray floret to 37 mm long and 10 mm wide near middle, base 2.5 mm wide; average size 35 mm long, 9 mm wide at center tapering to 2 mm wide at base; adaxial veins thickened and raised;

Ray floret color: Changing with maturity; when first horizontal young adaxial nearest RHS 16B, lightening to RHS 11C in mid-open period, and nearest RHS N155C proximally and between RHS 149D and RHS 145C at apex before dropping, basal 3 to 4 mm remaining constant between RHS 146A and RHS 146D in both adaxial and abaxial; abaxial beginning nearest RHS 4C when first horizontal, becoming nearest 4D in mid-open period, and nearest RHS 157C proximally with apex nearest RHS 149D before dropping;

Disk florets: About 400 to 450 per inflorescence; zygomorphic; perfect; produced in raised dome about 6.5 cm across and 5 cm tall, individually about 23 mm long and 9 mm wide;

*Disk floret corolla*.—Fused forming tube; to about 19 mm long and 9 mm wide at apex, fused in tube in basal 12 mm, free in distal 7 mm; individual tepals about 2.5 mm wide at fusion; acute apex; entire margin; both surfaces slightly lustrous.

*Disk floret corolla tube color*.—Adaxial and abaxial initially up opening nearest RHS 150C, becoming between RHS 18A and 18B both adaxial and abaxial, in late stage of flowering adaxial nearest RHS 18B and abaxial nearest RHS 18C.

*Androecium*.—Not observed on either ray florets or disk florets.

*Gynoecium*.—On ray florets only; single; to 5 mm long.

*Style*.—Single or split into up to five; to about 4 mm long and 0.2 mm diameter with shorter split styles of various lengths; color nearest RHS 155B.

*Stigma*.—Split into up to five; about 1 mm long and 0.1 mm diameter; color nearest RHS 15B.

*Fruit*.—Has not yet been observed.

Receptacle spines: With disk florets; acicular; glabrous; lustrous; to 11 mm long and 2 mm across near middle; producing a cone about 28 mm wide and 25 mm tall;

Spine color: With ray florets first horizontal apices nearest RHS 145A, center portion nearest 28A, and bases nearest RHS NN155C; mature flower apices and middle nearest RHS 183A, base between RHS 145D and RHS NN155C;

Disease resistance: Resistance and susceptibility beyond that of other hardy Coneflower cultivars have not been observed.

Growth: The plant grows best with plenty of moisture and adequate drainage but is able to tolerate some drought when mature.

Winter hardiness: at least from USDA zone 4 through 8.

I claim:

1. A new and distinct cultivar of *Echinacea* plant named 'Butter Pecan' as herein described and illustrated.

* * * * *